United States Patent [19]

Newbower et al.

[11] 4,236,527
[45] Dec. 2, 1980

[54] CARDIAC OUTPUT DETECTION BY MULTIPLE FREQUENCY THERMODILUTION

[75] Inventors: Ronald S. Newbower, Acton; James H. Philip, Chestnut Hill, both of Mass.

[73] Assignee: Massachusetts General Hospital, Boston, Mass.

[21] Appl. No.: 953,124

[22] Filed: Oct. 20, 1978

[51] Int. Cl.³ .............................................. A61B 5/02
[52] U.S. Cl. ...................................... 128/692; 73/204
[58] Field of Search ................................. 128/653–663, 128/691–694, 713; 73/204, 194 R, 194 E, 194 M

[56] References Cited

U.S. PATENT DOCUMENTS

| 3,498,128 | 3/1970 | Calvet | 73/204 |
| 3,595,079 | 7/1971 | Grahn | 73/204 |
| 3,719,083 | 3/1973 | Morris et al. | 73/204 |
| 3,995,623 | 12/1976 | Blake et al. | 128/349 R |

FOREIGN PATENT DOCUMENTS 1054763  1/1967  United Kingdom ...................... 73/204

OTHER PUBLICATIONS

Nealeigh, R. C. et al., "A Venous Pulse Doppler Catheter Tip Flowmeter for Measuring Arterial Blood Vel., Flow & Diam.," ISA Transactions, vol. 15, No. 1, pp. 84–87.
Hartley, C. J. et al., "A Single Crystal UTS Catheter Tip Velocity Probe," JAAMI, vol. 8, #4, Jul.–Aug. 1974, pp. 241–243.
Seed, W. A. et al., "Appl. of Const. Temp. Anemometry in Meas. of Intra-Arterial Blood Flow Vel.," Int. Jrnl. Engr. Sci., vol. 10, No. 12, Dec. 1972, pp. 1009–1021.
Runyan, R. A. et al., "Empir. Method for Freq. Comp. for Hot Wire Anemometer," NACA Tech. Note 1331, Jun. 1947.

Primary Examiner—Robert W. Michell
Assistant Examiner—Francis J. Jaworski
Attorney, Agent, or Firm—Weingarten, Maxham & Schurgin

[57] ABSTRACT

Method and apparatus for measuring cardiac output in which a traceable signal in the form of thermal energy or an injectate is applied to the blood flow through the heart having a plurality of frequency components with the traceable signal detected at a heart output vessel and analyzed at the plural frequency components to provide cardiac output rate and ejection fraction information. The traceable signal is preferably heat energy applied as a very low frequency modulation of a high frequency signal at a fundamental and further harmonic or as a square wave in which multiple harmonics are present. At least two frequency components of the square wave are then separately analyzed. A multiple frequency system in addition to permitting analysis of previously undetectable heart output characteristics additionally permits determination of whether the source of the traceable signal is properly located within the heart such as in the ventricle.

14 Claims, 9 Drawing Figures

CARDIAC OUTPUT DETECTION BY MULTIPLE FREQUENCY THERMODILUTION

FIELD OF THE INVENTION

The present invention relates to the monitoring of cardiac output characteristics by the injection of a signal within the heart and monitoring of its response at the heart output.

BACKGROUND OF THE INVENTION

Heart output flow rate monitoring is important in the care of many critically ill patients. A known technique for measuring heart output characteristics operates by injecting into the heart ventricle or other location a time varying signal, such as heat. The signal or indicator may be an injected fluid or heat change. Downstream of the injection point, preferably at an output artery in the case of the right heart, a sensor for the injected signal, such as a thermistor electrical conductivity gauge, etc. is placed to measure the magnitude and time of appearance of the injected signal. This known technique permits monitoring of relative heart flow rate on the principal that the greater the flow, the greater will be the dilution of the indicator and therefore the lower will be the magnitude of the sensed indicator or traceable signal at the point of monitoring. Thus variations in heart output rate can be measured on this principle.

Among the approaches to heart rate monitoring, that of adding heat through an electrically energized element in the heart has the attraction of simplicity and precise regulation of the injected power. It has, however, until recently not achieved widespread acceptance due to the potential damage from local overheating necessitated by the high power levels which must be used to overcome a highly disadvantageous signal-to-noise ratio. Accordingly, standard techniques have involved the injection of a dilutable conductive or cold fluid. More recently it has been determined that the signal-to-noise ratio can be vastly improved by driving the heater element at a frequency corresponding to a minimal noise frequency in the blood flow circuit. This permits reduction in the applied power levels while maintaining sufficient sensitivity to provide a usable cardiac output figure.

This technique is limited to measuring relative values of cardiac output due to the presence of an unknown factor in the transfer function which relates the injection signal to its monitored value. This unknown is the filtering effect of the mixing volume of the heart and blood flow chambers depending further upon the precise location of the indicator source. Knowledge of these variables by themselves is significant to patient care and would furthermore permit greater accuracy and reliability in the measured heart output rate.

SUMMARY OF THE INVENTION

In accordance with the teaching of the present invention, method and apparatus are provided in which cardiac output is monitored to provide output rate, information on indicator source position, and indicator mixing volume i.e. heart chamber volume. This information, coupled with heart beat rate, provides an indication of the actual ejection fraction in each heart beat which in turn provides an indication of heart condition.

This additional information is obtained by applying an indicator or traceable signal in the form of thermal energy or an injectate to the blood stream near or in the heart. The signal is modulated at plural frequencies such as by first and a further harmonic or by the application of a repeating square wave. The fundamental frequency of the indicator modulation is preferably selected at a noise minimum in the cardiac system noise profile and this frequency is monitored separately from the other frequencies in the applied indicator to yield conventional cardiac output information. A further frequency is then monitored, or square wave rise time is detected in the heart output conduit, normally the pulmonary artery in the case of the right heart frequently employed for cardiac output detection. This additional analysis permits detection of the second variable affecting the transfer function between the indicator injection and downstream sensing and permits the complete transfer function to be determined. This in turn permits not only relative heart output, but absolute heart output or ejection fraction to be determined in combination with easily detected heart beat rate. It additionally provides a measure of heart volume and location of the indicator source which in most applications is preferably positioned within the ventricle.

DESCRIPTION OF THE DRAWING

These and other features of the present invention are more fully set forth below in the solely exemplary detailed description of the invention and in the accompanying drawing of which.

DETAILED DESCRIPTION OF THE INVENTION

The present invention contemplates a cardiac output monitor in which a traceable signal in the form of thermal energy or an injectate or indicator is applied in the heart and monitored at the heart output at plural frequencies in order to permit resolution of the plural variables affecting the cardiac transfer function between indicator injection and detection. This permits analysis of cardiac output in absolute terms including output rate and, knowing rate, the heart ejection fraction. In addition proper placement of the indicator source can be determined.

Figure 1:
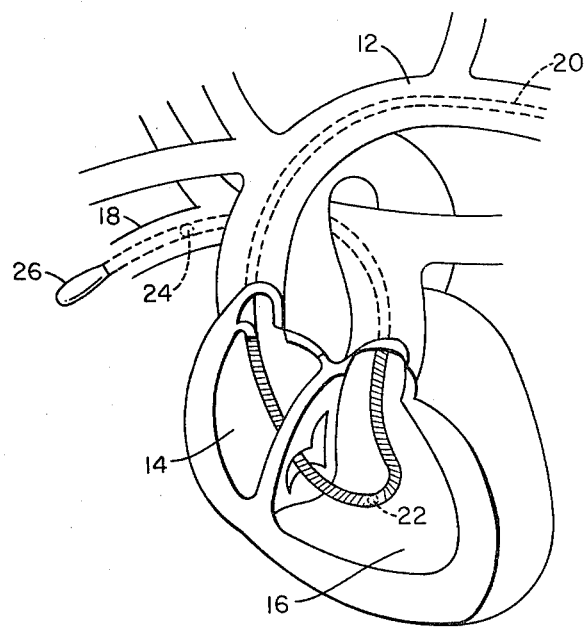
FIG. 1 is a partially cut away plan view of a typical human heart.
Figure 2A:
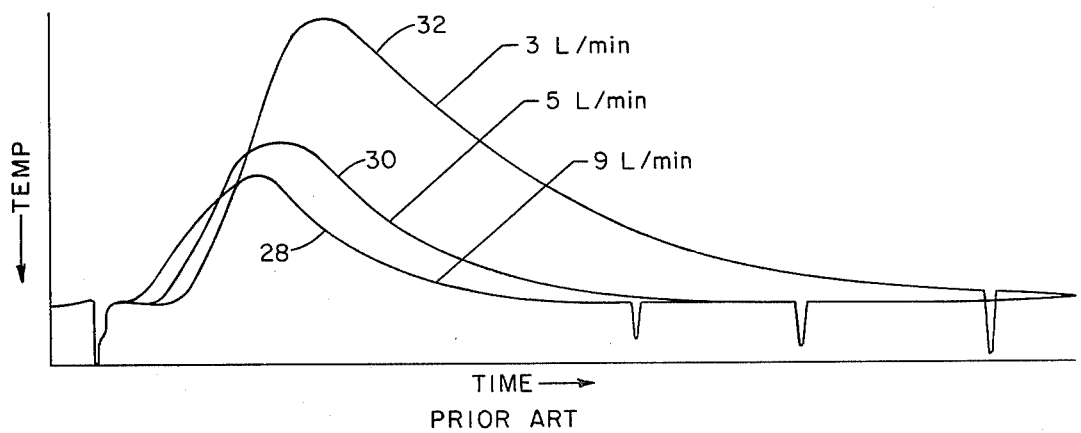
FIGS. 2A & B are waveform diagrams illustrating data obtained by prior art cardiac output thermodilution techniques.
Figure 2B:
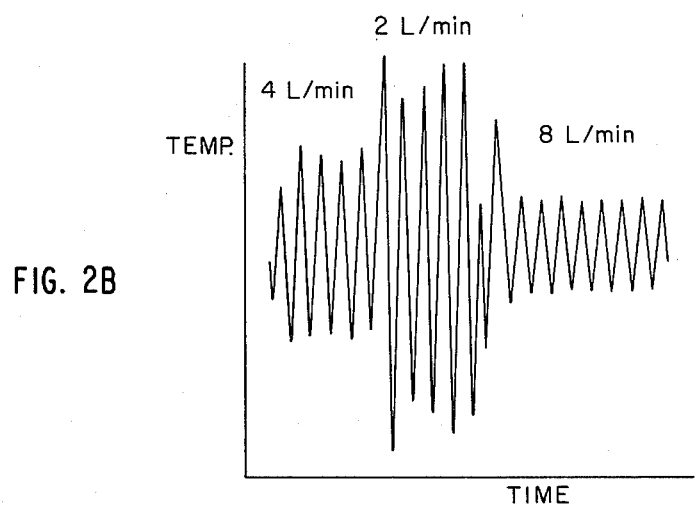

With reference to FIG. 1 the location of a catheter in the right heart and pulmonary artery for use in the present invention, is illustrated in partial cut away view. As shown there a catheter 20 is inserted through the vena cava 12 to the right auricle 14 and thence through the right ventricle 16 into the pulmonary artery 18. The catheter 20 consists of a flexible cable having an injection site 22 such as a resistance heater to provide heat to the blood flowing through the heart. Other sources of indicator may be used, for example the injection of a hot or cold fluid or of a solution having an electrical conductivity different from that of the blood fluid. The catheter has an indicator sensor 24 which in the case of thermodilution includes a thermistor. The cables for the indicator source and detector are contained within the catheter 20. To facilitate insertion of the catheter it is preferably terminated with a balloon 26 inflatable through tubing in the catheter 20 to cause the balloon tip 26 to be drawn through the cardiac system including the heart and to exit through the pulmonary artery. The indicator source 22 is illustrated as present within the right ventricle. Other locations may be utilized intentionally or occur accidentally Systems of this type have been utilized in the past and effectively provide an indication of variation in cardiac output or blood flow rate. FIG. 2A shows the response of one prior art system where cardiac output temperature change is shown in response to an injected impulse of cold fluid at three flow rates. FIG. 2B shows response in the case of different flow rates with a sine-wave indicator injection. As may be seen from FIGS. 2A & 2B, with increasing flow rate, a greater volume of blood passes the injection site per unit of time thereby more greatly reducing the concentration or increasing the dilution of the indicator such that while it arrives sooner at the monitor site 24 it produces a lower net deviation in temperature, salinity etc. A family of curves 28, 30 and 32 illustrate this progressive change from higher to lower relative flow rates.

One variable which differs from patient to patient affects the measurement of cardiac output. This is fluid capacity, or mixing volume, of the vessels and chambers between the injection and monitoring sites. This variable may not be readily detected, and its uncertainty precludes the determination of absolute cardiac output particularly at low values of output as well as the heart ejection fraction, the actual portion of blood ejected with each heart beat.

Figure 3:
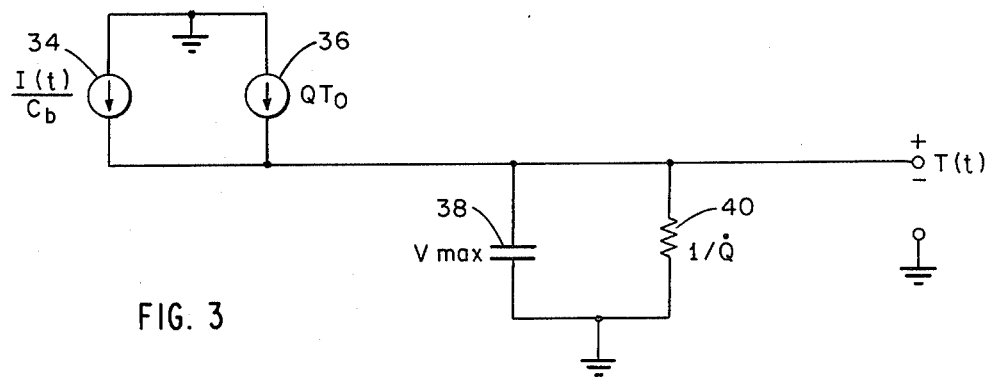
FIG. 3 is an equivalent circuit diagram of a heart transfer function for indicator injection to detection.

To visualize and appreciate the inaccuracies in measured cardiac output using prior art techniques, reference is made to FIG. 3 showing an electrical, approximate equivalent circuit for the cardiac transfer function from injected indicator to detected indicator. The equivalent circuit includes a current source 34 which corresponds to the injected heat divided by the specific heat-specific gravity product of blood. In parallel with this current source is a current source 36 corresponding to the cardiac flow rate, $\dot{Q}$, multiplied by the base line temperature of the blood. These inputs are applied to the heart equivalent circuit represented by a capacitor 38 closely corresponding to the volume (End-Diastolic) of the right ventricle in parallel with a loss element 40 having the value $1/\dot{Q}$ representative of the flow from the heart. The potential across the element 40 corresponds to the temperature in the output stream. The equation describing this function is $$\dot{Q}T_o + \frac{I(t)}{C_b} = \dot{Q}T(t) + V_{max} \times \frac{dT(t)}{dt}$$

As can be seen from this equation the variables $I(t)$, $C_b$, $T_o$ may all be readily determined or known in advance. The variable $T(t)$ is measured at the detection site. The End-Diastolic volume $V_{max}$ is not known and is known to vary even within the same patient. This variation introduces an uncertainty in monitored cardiac output, $\dot{Q}$, which increases as $V_{max}$ increases or $\dot{Q}$ decreases.

Figure 4:
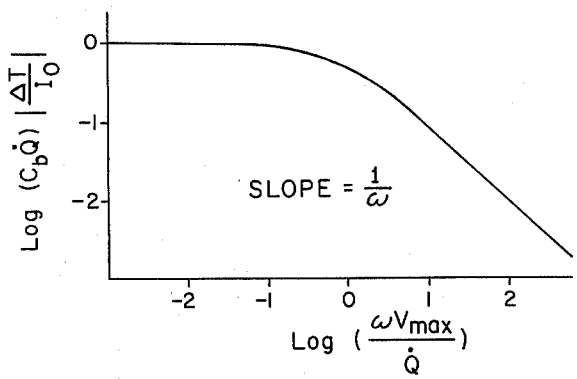
FIG. 4 is a waveform diagram illustrating the transfer function response curve for the heart to injected indicator as detected by a sensor at the heart output.

With reference to FIG. 4 a plot of the normalized transfer function governed by the model of FIG. 3 is illustrated. For a constant $V_{max}$ and an individual catheter installation, a measured temperature at the monitor site will determine a point on the curve of FIG. 4 but there is no way that the location of that point along the curve may be determined. A determination of the saturation level of or another point on the curve of FIG. 4, will precisely locate the curve and permit a determination of the actual transfer function.

Figure 5:
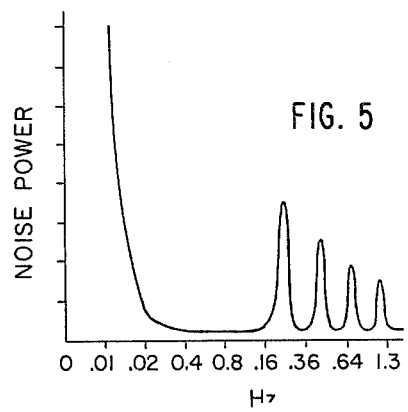
FIG. 5 is a waveform diagram of cardiac noise versus frequency.

The function $I(t)$ has in the prior art taken various forms, more recently a single frequency sinusoidal waveform of very low, less than one Hz, frequency. This has been determined to be advantageous from a noise analysis of the noise spectrum of the normal cardiac system as illustrated in FIG. 5. As shown there, a substantial noise minimum occurs in the range of approximately 0.02–0.1 Hz and it has therefore been proposed in the past to drive and detect the injector at a frequency in this range to minimize noise.

What is more significant from the standpoint of the present invention is the appreciation that the location of the noise minimum typically spans nearly three octaves permitting plural, well separated frequencies to be used simultaneously to inject indicator or indeed to apply the indicator in a repeating square wave. The present invention uses separate frequencies of indicator modulation and detects the indicator response at the detection site at each frequency or as a function of the plural frequencies separately. This permits additional information to be obtained which compensates for the unknown volume factor in the equation or indeed permits its determination so that the transfer is or can be completely determined for example by fitting two points to the curve of FIG. 4. If the data fit the curve of FIG. 4 at an abnormal position, it typically indicates an improperly positioned catheter such as, for example, the failure of the indicator injection site to be located within the right ventricle.

Figure 6:
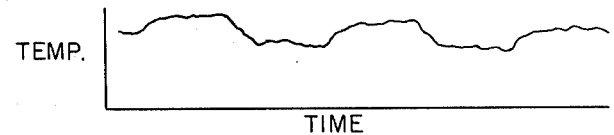
FIG. 6 is a waveform diagram of a recovered square wave in accordance with the present invention.

In the case of the square wave driving function the detected signal, as shown in FIG. 6, is filtered at the fundamental frequency of the square wave and peak detected to provide a relative flow rate figure as has been previously available. Peak detection may be by actual peak measurement, by cross-correlation, or by other known techniques of peak or amplitude detection. In addition, the rise time of the square wave as it appears at the detector site is also determined, for example using known signal processing techniques. With the rise time known, the location of the equivalent circuit pole of the curve of FIG. 4 is known (its frequency is the reciprocal of the rise time) and the detected first harmonic amplitude can be matched to the curve of FIG. 4 to locate at its known frequency the entire transfer function. In a case where two distinct frequencies of indicator are employed, the first frequency is again processed as indicated above and the second is also filtered and peak detected. The two relative values of these variables may be placed upon the FIG. 4 curve using known curve fitting techniques to thereby also scale the curve of FIG. 4 to the actual conditions monitored. It should be noted that with a square wave indicator injected, detection at two separate, frequencies may also be used.

Where rise time exceeds certain normal values significantly or where the two independent frequency signals fit the curve beyond the normal range, it is an indication of misplacement of the injector site, as for example in the right auricle rather than right ventricle. Even so, the use of the multiple frequency technique permits a more accurate determination of the actual transfer function from the injector site to the monitoring site.

Figure 7:
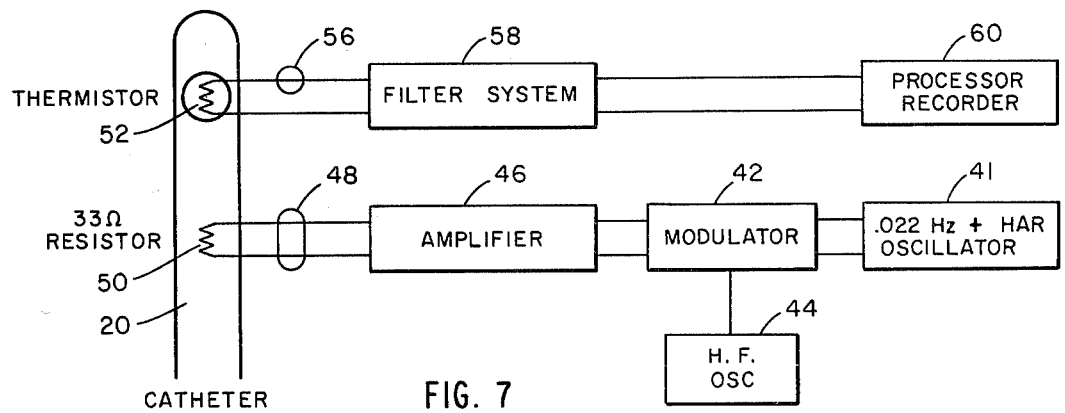
FIG. 7 is a block diagram of circuitry for use in applying and recovering multiple frequency trace indicator in cardiac output measuring.

With respect now to FIG. 7 circuitry for use in implementing the present invention is presented. An oscillator 41 is provided having multiple frequency characteristics such as a fundamental and harmonic frequency or square wave pattern. This is preferably applied to a modulator 42 to modulate a high frequency from a high frequency oscillator 44 to minimize the myocardial effects of inadvertent leakage currents. The modulated high frequency signal is amplified by an amplifier 46 and applied through cables 48 of the catheter to a low value, such as 33 ohm resistor 50 at the injection site in the catheter 20. Near the tip of the catheter 20, a thermistor 52 is provided having a resistance varying as a function of temperature. The thermistor 52 is energized by a source 56 which applies current through the thermistor and variations in thermistor response are applied through a filter system 58, typically a one or higher order pole filter, which selectively and separately passes the fundamental and other frequences of interest to a processor and recorder system 60 to provide the electrical signal processing.

Figure 8:
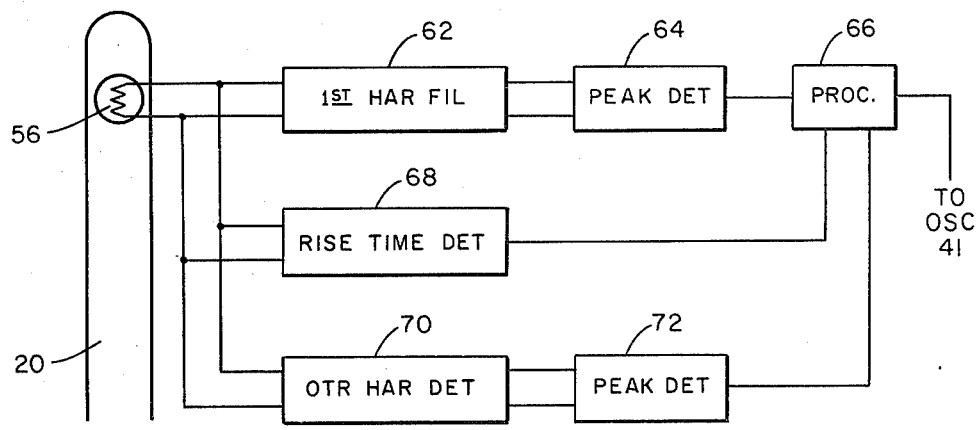
FIG. 8 is a more detailed block diagram of multiple frequency signal analysis in accordance with the present invention.

With respect to FIG. 8, the details of signal processing are more fully shown. The output of the thermistor 52 is applied through a first harmonic filter 62 which selectively passes only the first harmonic in the modulating frequency from the oscillator 41. The magnitude of this signal, is applied to a peak detector 64. The peak detector 64 normally receives an input in the form similar to the waveforms of FIG. 2B and provides an output signal corresponding to the peak value of that input using techniques known in the art. This peak value is applied to a processing system 66 for automated curve fitting where desired.

In the case of square wave drive signals, the response of the thermistor 56 is, in one embodiment, applied through a rise time detector 68 such as a triggered timer and its output, representing the rise time of, for example, the waveforms illustrated in FIG. 6, is applied to the processor 66.

In the second embodiment of a square wave drive signal or where two distinct sinusoidal frequency modulations are employed, the output of thermistor 56 is alternatively applied through a filter 70 selectively passing the other frequency, typically a harmonic of the fundamental, to a further peak detector 72 which in turn provides an output representing the peak of the applied signal. This signal is in turn applied to the processor 66. The processor 66 operates in accordance with the above identified theory where the fundamental peak and rise time are provided to detect the pole frequency of the heart equivalent circuit, then fit the curve to the detected amplitude of the detected first harmonic with the pole defining the frequency base on the curve. In the case where the peak values of two independent frequencies are employed, these values are spaced by their known frequencies, and fitted to the curve based on their amplitude differences, again using known curve fitting techniques.

The above description is of a preferred form for practicing multiple frequency cardiac output detection and is not intended to be limited to the specific structure shown for its implementation. Accordingly, the scope of the invention is to be limited only as represented by the following claims.

What is claimed is:

1. Apparatus for cardiac thermodilution measurement comprising:
   means for applying a traceable signal by injection of thermal energy for dilution in the blood flow in a location upstream of a heart output conduit;
   means for varying the magnitude of the traceable signal as a function of time at at least two frequencies thereby varying the amount of thermal energy applied to the blood flow;
   means for detecting said traceable signal as blood flow temperature downstream of the heart ventricle at the first of said at least two frequencies; and
   means for separately detecting at least the second of said at least two frequencies in said traceable signal as blood flow temperature downstream of the ventricle of said heart.

2. The process of claim 1 wherein:
   said step of detecting said first frequency includes the step of detecting the peak value of said traceable signal at said first frequency;
   said step of detecting at least said second frequency includes the step detecting the peak value of said traceable signal at said second frequency.

3. The process of claim 2 further including the step of determining the cardiac transfer function between sites of application of the traceable signal and of its detection.

4. The process of claim 1 wherein:
   the signal applying step includes the step of applying a square wave signal;
   the first frequency is the fundamental frequency of said square wave signal and;
   said at least second frequency is multiple harmonics above said first frequency.

5. The process of claim 4 wherein said step of detecting the traceable signal at said at least second frequency includes the step of detecting the square wave rise time.

6. The process of claim 5 further including the step of determining the cardiac transfer function between sites of application of the traceable signal and of its detection.

7. The process of claim 6 wherein said step of detecting the first frequency of said traceable signal includes the step of peak detecting said signal at said first frequency.

8. The process of claim 4 wherein said separate detecting step includes detecting the peak value of at least one frequency of said multiple harmonics.

9. The process of claim 1 wherein said step of applying first and at least a second frequency of a traceable signal includes the step of modulating a frequency higher than said first and at least second frequencies at the rates of said first and at least second frequencies.

10. The process of claim 1 wherein said step of applying said traceable signal includes the step of applying said traceable signal to a heart ventricle.

11. A process for detecting pump output characteristics in a pump of the type having a chamber of reducible volume which is periodically reduced and expanded in a cyclical fashion at a known rate along with inlet and outlet conduits and corresponding valves to promote the flow of a fluid material in a predetermined direction from said inlet to said outlet conduit, a process for detecting flow characteristics comprising:

applying a traceable signal in the form of thermal energy or an injectate varying in magnitude at a first and at least a second distinct frequency to the reducible volume of said chamber at a first location to mix with and be diluted by said fluid material;

detecting in said outlet at a second location downstream of said first location said traceable signal as mixed with and diluted by said fluid material at said first frequency;

detecting in said outlet conduit said traceable signal as mixed with and diluted by said fluid material at at least second frequency.

12. Apparatus for cardiac thermodilution measurement comprising:

means for applying a traceable signal by injection of thermal energy for dilution in the blood flow in a location upstream of a heart output conduit;

means for varying the magnitude of the traceable signal as a function of time at at least two frequencies thereby varying the amount of thermal energy applied to the blood flow;

means for detecting said traceable signal as blood flow temperature downstream of the heart ventricle at the first of said at least two frequencies; and means for separately detecting at least the second of said at least two frequencies in said traceable signal as blood flow temperature downstream of the ventricle of said heart.

13. A process for detecting flow output characteristics of a fluid material through a chamber with a mixing volume having an outlet conduit, said process for detecting flow output characteristics comprising:

applying a traceable signal in the form of thermal energy or an injectate varying in magnitude at a first and at least a second distinct frequency to the mixing volume of said chamber;

detecting in said outlet conduit at a second location downstream of said first location said traceable signal as mixed with and diluted by said fluid material at said first frequency;

detecting in said outlet conduit said traceable signal as mixed with and diluted by said fluid material at at least said second frequency.

14. A process for detecting pump output characteristics in a pump of the type having a chamber of reducible volume which is periodically reduced and expanded in a cyclical fashion at a known rate along with inlet and outlet conduits and corresponding valves to promote the flow of a fluid material in a predetermined direction from said inlet to said outlet conduit, a process for detecting flow characteristics comprising:

applying a traceable signal in the form of thermal energy or an injectate varying in magnitude at a first and at least a second distinct frequency to the reducible volume of said chamber at a first location to mix with and be diluted by said fluid material;

detecting in said outlet conduit at a second location downstream of said first location said traceable signal as mixed with and diluted by said fluid material at said first frequency;

detecting in said outlet conduit said traceable signal as mixed with and diluted by said fluid material at at least second frequency.

* * * * *

UNITED STATES PATENT AND TRADEMARK OFFICE
CERTIFICATE OF CORRECTION

PATENT NO. : 4,236,527
DATED : December 2, 1980
INVENTOR(S) : Ronald S. Newbower, et al It is certified that error appears in the above—identified patent and that said Letters Patent is hereby corrected as shown below:

Column 8, line 33, "at least second frequency." should read —at least said second frequency.—

Signed and Sealed this

Sixteenth Day of June 1981

[SEAL]

Attest:

RENE D. TEGTMEYER

Attesting Officer   Acting Commissioner of Patents and Trademarks

UNITED STATES PATENT AND TRADEMARK OFFICE
CERTIFICATE OF CORRECTION

PATENT NO. : 4,236,527
DATED : December 2, 1980
INVENTOR(S) : Ronald S. Newbower et al It is certified that error appears in the above—identified patent and that said Letters Patent is hereby corrected as shown below:

Column 4, line 39, "the transfer is" should read
--the transfer function is--.

Signed and Sealed this

Tenth Day of November 1981

[SEAL]

Attest:

GERALD J. MOSSINGHOFF

Attesting Officer       Commissioner of Patents and Trademarks

UNITED STATES PATENT AND TRADEMARK OFFICE
CERTIFICATE OF CORRECTION

PATENT NO. : 4,236,527
DATED : December 2, 1980
INVENTOR(S) : Ronald S. Nebower, et al.

It is certified that error appears in the above-indentified patent and that said Letters Patent is hereby corrected as shown below:

Column 1, before "FIELD OF THE INVENTION" please add --This invention was made with government support under Grant No. GM15904 awarded by the Department of Health and Human Services. The government has certain rights in this invention.--

Column 6, line 8, "Apparatus for" should read --A method of --;

Column 6, line 10, delete "means for";

Column 6, line 13, delete "means for";

Column 6, line 17, delete "means for";

Column 6, line 20, delete "means for";

Signed and Sealed this

Fourteenth Day of March, 1995

Attest:

BRUCE LEHMAN

Attesting Officer

Commissioner of Patents and Trademarks